(12) United States Patent
Jiang et al.

(10) Patent No.: US 10,127,835 B2
(45) Date of Patent: Nov. 13, 2018

(54) CAPACITIVE TOUCH SENSOR

(71) Applicant: Wisconsin Alumni Research Foundation, Madison, WI (US)

(72) Inventors: Hongrui Jiang, Madison, WI (US); Jayer A. Fernandes, Madison, WI (US)

(73) Assignee: Wisonsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/427,272

(22) Filed: Feb. 8, 2017

(65) Prior Publication Data

US 2018/0225990 A1 Aug. 9, 2018

(51) Int. Cl.
*H03K 17/975* (2006.01)
*G09B 23/28* (2006.01)
*H03K 17/96* (2006.01)

(52) U.S. Cl.
CPC ........... *G09B 23/28* (2013.01); *H03K 17/962* (2013.01)

(58) Field of Classification Search
CPC ...... G09B 23/28; H03K 17/962; H01H 13/00; H01H 13/02; H01H 13/14; H01H 13/26; H01H 13/28; H01H 13/50; H01H 13/70; H01H 13/702; H01H 13/703; H01H 13/704; H01H 13/705; H01H 15/00; H01H 15/02; H01H 2003/12; H01H 2205/002; H01H 2205/01; H01H 2205/00; H01H 2221/00; H01H 2221/008; H01H 2221/01; H01H 2221/012; H01H 2221/032; H01H 2239/074; H01H 1/00; H01H 1/12; H01H 1/18; H01H 1/36; H01H 1/226; H01H 3/00; H01H 3/12; H01H 5/00; H01H 5/04;

(Continued)

(56) References Cited

U.S. PATENT DOCUMENTS 7,609,178 B2 * 10/2009 Son .................... G06F 3/016
 200/600
8,544,325 B2 10/2013 Ackerley et al.
(Continued)

FOREIGN PATENT DOCUMENTS

WO 2014068269 5/2014

OTHER PUBLICATIONS

Kwan et al., "Validity of a Newly Developed Tri-axial Sensor for Clinical Breast Examination Skills Assessment", Stud Health Techno Inform, vol. 196, pp. 225-229, 2014.

(Continued)

*Primary Examiner* — Anthony R. Jimenez (74) *Attorney, Agent, or Firm* — Boyle Fredrickson, S.C.

(57) ABSTRACT

A capacitive touch sensor is provided, The capacitive touch sensor includes a plate having an upper surface and lying in a plate plane. A generally planar, first electrode is spaced from the plate along an axis generally perpendicular to the upper surface of the plate. The first electrode movable with respect to the plate in response to a force. A plurality of second electrodes are interconnected to the plate and circumferentially spaced about the axis. Each of the plurality of the second electrodes has a corresponding differential capacitance with the first electrode. The differential capacitances between the first electrode and the plurality of second electrodes vary in the response to the movement of the first electrode.

22 Claims, 6 Drawing Sheets

(58) Field of Classification Search
CPC ..... A61B 5/447; A61B 5/6894; A61B 5/6892; A61B 5/6807; A61F 2/80; A61F 2/70
USPC .......................................... 200/600, 237, 238
See application file for complete search history.

(56) References Cited

U.S. PATENT DOCUMENTS

| | | | |
|---|---|---|---|
| 2009/0057124 A1* | 3/2009 | Orsley | G06F 3/0338 200/600 |
| 2012/0092263 A1* | 4/2012 | Peterson | G06F 3/016 345/168 |
| 2016/0015311 A1 | 1/2016 | Jiang | |

OTHER PUBLICATIONS

Chiang et al., "An implantable capacitive pressure sensor for biomedical applications", Sensors and Actuators A: Physical, vol. 134, No. 2, pp. 382-388, 2007.

Lai et al., "A flexible tactile sensing array for robot applications", Sensors, 2010 IEEE, Nov. 2010, pp. 2599-2602.

Charalambides et al., "A novel all-elastomer mems tactile sensor for high dynamic range shear and normal force sensing", Journal of Micromechanics and Microengineering, vol. 25, No. 9, p. 095009.

Mannsfeld et al., "Highly sensitive flexible pressure sensors with microstructured rubber dielectric layers", Nature matierals, No. 10, pp. 859-864, October.

Chase et al., "A thin-fil flexible capacitive tactile normal/shear force array sensor", Industrial Electronics, Control, and Instrumentation, 1995, Proceedings of the 1995 IEEE IECON 21st International Conference, vol. 2, No. 1995, pp. 1196-1201.

Murakami et al., "Feasibility of novel four degrees of freedom capacitive force sensor for skin interface force", Biomed Eng Online, 2012; 11:90.

"Sensor Pad and Software for Training Doctors in Breast Examinations", Right Hand Technologies, www.righthandtech.com/projects-mammacare-sensor.php, 2 pages.

Baxter, "Capacitive Sensors", www.capsense.com/capsense-wp.pdf, 2000, 17 pages.

* cited by examiner

CAPACITIVE TOUCH SENSOR

FIELD OF THE INVENTION

This invention relates generally to capacitive touch sensors, and in particular, to a flexible, three-axis, capacitive touch sensor that is capable of resolving normal pressure and tracking directional motion.

BACKGROUND AND SUMMARY OF THE INVENTION

As is known, physicians rely heavily on their ability to use tactile feedback during a clinical breast examination (CBE) in order to determine the presence of lumps, nodules and other tissue abnormalities that might be indicative of breast cancer. These types of examinations often include soft and hard presses of tissue to feel depth and palpations and squeezes of the tissue to feel the extent of the tissue's, mass. Hence, in order to properly tram medical residents to conduct a CBE properly, training systems incorporating touch sensing technology have been developed.

As is known, touch sensing technology is used in a variety of electronic products, including medical devices. In these types of training systems, it is highly desirable for the sensor to have the ability to track normal pressure exerted by a force, as well as, the direction and locus of movement of the force. For example, the force may take the form of a hand of the physician during examination of a breast. However, current sensing solutions available to physicians are based on piezoelectric sensing schemes and are capable of measuring only normal pressure over a large area, but not directional changes. As a result, the sensors in current training systems are incapable of tracking motions, e.g. circular motions, which are critical to determine the size of a lump. Further, these sensors in current training systems also show hysteresis and are susceptible to drift due to temperature variations and external vibrations.

In order to overcome the challenges associated with piezoelectric sensing schemes in current naming systems, the use of capacitive touch sensor technology has been explored. A capacitive sensing solution is preferred because of its high sensitivity, low power consumption and low drift. Prior work in the area of flexible capacitive sensors has mainly focused on the electrode design for robotic tactile sensing. These capacitive sensors utilize a thin layer of an elastomer, e.g. polydimethylsiloxane (PDMS) or Ecoflex, as a dielectric layer, whose compression allows for the limited measurement of normal forces, and displacement allows for the measurement of shear to some extent. Deformation of an elastomeric thin film subjects the types, of capacitive sensors to intrinsic mechanisms, which results in long relaxation times after compression.

Therefore, it is a primary object and feature of the present invention to provide a flexible, three-axis, capacitive touch sensor that is capable of resolving normal pressure to and tracking directional motion.

It is a further object and feature of the present invention to provide a flexible, three-axis, capacitive touch sensor that deforms easily and allows for a quick recovery from the deformation so as to improve the sensitivity thereof.

It is a still further object and feature of the present invention to provide a flexible, three-axis, capacitive touch, sensor that is simple and inexpensive to manufacture.

In accordance with the present invention, a capacitive touch sensor is provided. The capacitive touch sensor includes a plate having an upper surface and lying in a plate plane. A generally planar, first electrode is spaced from the plate along an axis generally perpendicular to the upper surface of the plate. The first electrode movable with respect to the plate in response to a force. A plurality of second electrodes are interconnected to the plate and circumferentially spaced about the axis. Each of the plurality of the second electrodes having a corresponding differential capacitance with the first electrode. The differential capacitances between the first electrode and the plurality of second electrodes vary in the response to the movement of the first electrode.

A dielectric layer extends between the plate and the first electrode and includes a plurality of dielectric posts. The dielectric posts flex in a direction corresponding to a direction of the force applied to the first electrode. Each of the plurality of second electrodes is generally flat and lies in an electrode plane generally parallel to the plate plane. Each of the plurality of second electrodes has a generally square configuration. At least a portion of the first electrode is moveable in an x-direction, a y-direction and a z-direction, wherein: the y-direction is generally parallel to axis; the x-direction is generally perpendicular to the y-direction; and the z-direction is generally perpendicular to the x-direction and the y-direction.

In accordance with a further aspect of the present invention, a capacitive touch sensor is provided. The capacitive touch sensor includes a plate lying in a plate plane having a first set of electrodes supported on an upper surface thereof. Each electrode of the first set of electrodes is circumferentially spaced about an axis extending through the plate and is perpendicular to the upper surface. A generally planar, first electrode is spaced from the plate along the axis. The first electrode is movable with respect to each electrode of the first set of electrodes in response to a force and has a corresponding differential capacitance with each electrode of the first set of electrodes. The differential capacitances between the first electrode and each electrode of the first set of electrodes varies in the response to the movement of the first electrode.

A dielectric layer extends between the plate and the first electrode, and includes a plurality of dielectric posts. The dielectric posts flex in a direction corresponding to a direction of the force applied to the first electrode. Each electrode of the first set of electrodes is generally flat and lies in an electrode plane generally parallel to the plate plane. Each electrode of the first set of electrodes has a generally square configuration. At least a portion of the first electrode is moveable in an x-direction, y-direction and a z-direction, wherein: the y-direction is generally parallel to axis; the x-direction is generally perpendicular to the y-direction; and the z-direction is generally perpendicular to the x-direction and the y-direction.

In accordance with a still further aspect of the present invention, a method of tracking pressure exerted by and a locus of movement of a force is provided. The method includes the step of exerting a pressure on a sensor with the force. The sensor has a variable differential capacitance. The differential capacitance is varied in response to at least one of the pressure exerted by the force on the sensor and a locus of movement of the force along the sensor.

The sensor includes a plate having an upper surface and lying in a plate plane. A generally planar, first electrode is spaced from the plate along an axis generally perpendicular to the upper surface of the plate. The first electrode is movable with respect to the plate in response to a force. A plurality of second electrodes are interconnected to the plate and are circumferentially spaced about the axis. Each of the plurality of the second electrodes has a corresponding differential capacitance with the first electrode. The differential capacitances between the first electrode and each of the plurality of second electrodes vary in response to at the pressure exerted by the force on the first electrode and/or in response to the locus of movement of the force along the first electrode.

The sensor also includes a dielectric layer extending between the plate and the first electrode and includes a plurality of dielectric posts. The dielectric posts flex in a direction corresponding to at least one of the pressure exerted by the force on the first electrode and the locus of movement of the force along the first electrode. At least a portion of the first electrode is moveable in an x-direction, a y-direction and a z-direction, wherein: the y-direction is generally parallel to axis; the x-direction is generally perpendicular to the y-direction: and the z-direction is generally perpendicular to the x-direction and the y-direction.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
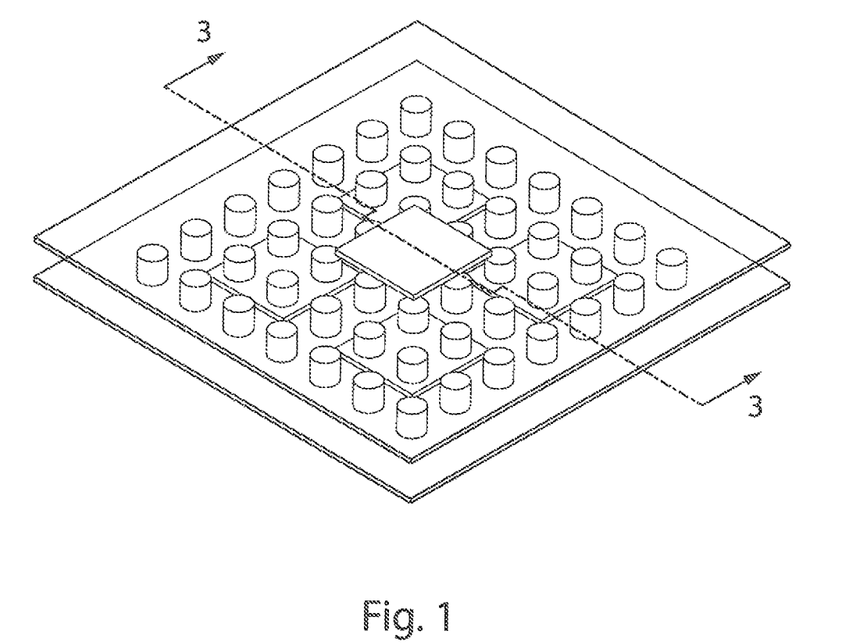
FIG. 1 is schematic, isometric view of a capacitive touch sensor in accordance with the present invention.
Figure 3:
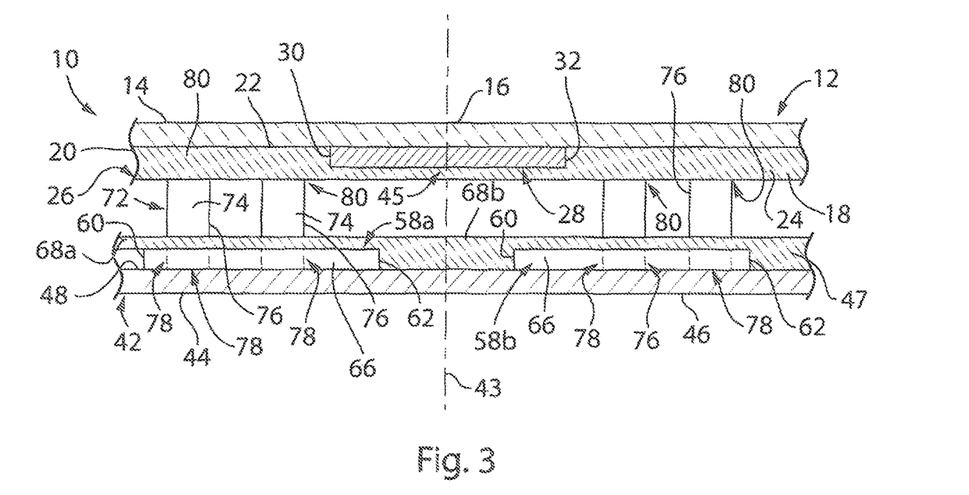
FIG. 3 is a cross-sectional view of the capacitive touch sensor of the present invention taken along line 3-3 of FIG. 1.

Referring to FIGS. 1 and 3, a capacitive touch sensor in accordance with the present invention is generally designated by the reference numeral 10. Touch sensor 10 includes an upper plate 12 is defined by base layer 14 fabricated from an insulating material. Base layer 14 includes an outer surface 16 and an inner surface 18. Copper layer 20 includes a first surface 22 bonded to inner surface 18 of base 14 in any conventional matter and an second surface 24. Copper layer 20 defines a first electrode 28 is formed in upper plate 12 and line 38 extending therefrom. More specifically, first electrode 28 is defined by first and second sides 30 and 32, respectively, and first and second ends, 34 and 36, respectively. In the depicted embodiment, first electrode 28 has a square configuration. However, other configurations are possible, e.g, a circular configuration, without deviating from the scope of the present invention. Line 38 interconnects terminal 40 and first electrode 28. Terminal 40 is provided adjacent outer periphery 41 of upper plate 12 for reasons hereinafter described. Insulating coverlay 26 is provided over second surface 24 and copper layer 20 to prevent short circuits during operation of touch sensor 10, hereinafter described.

Figures 5, 6:
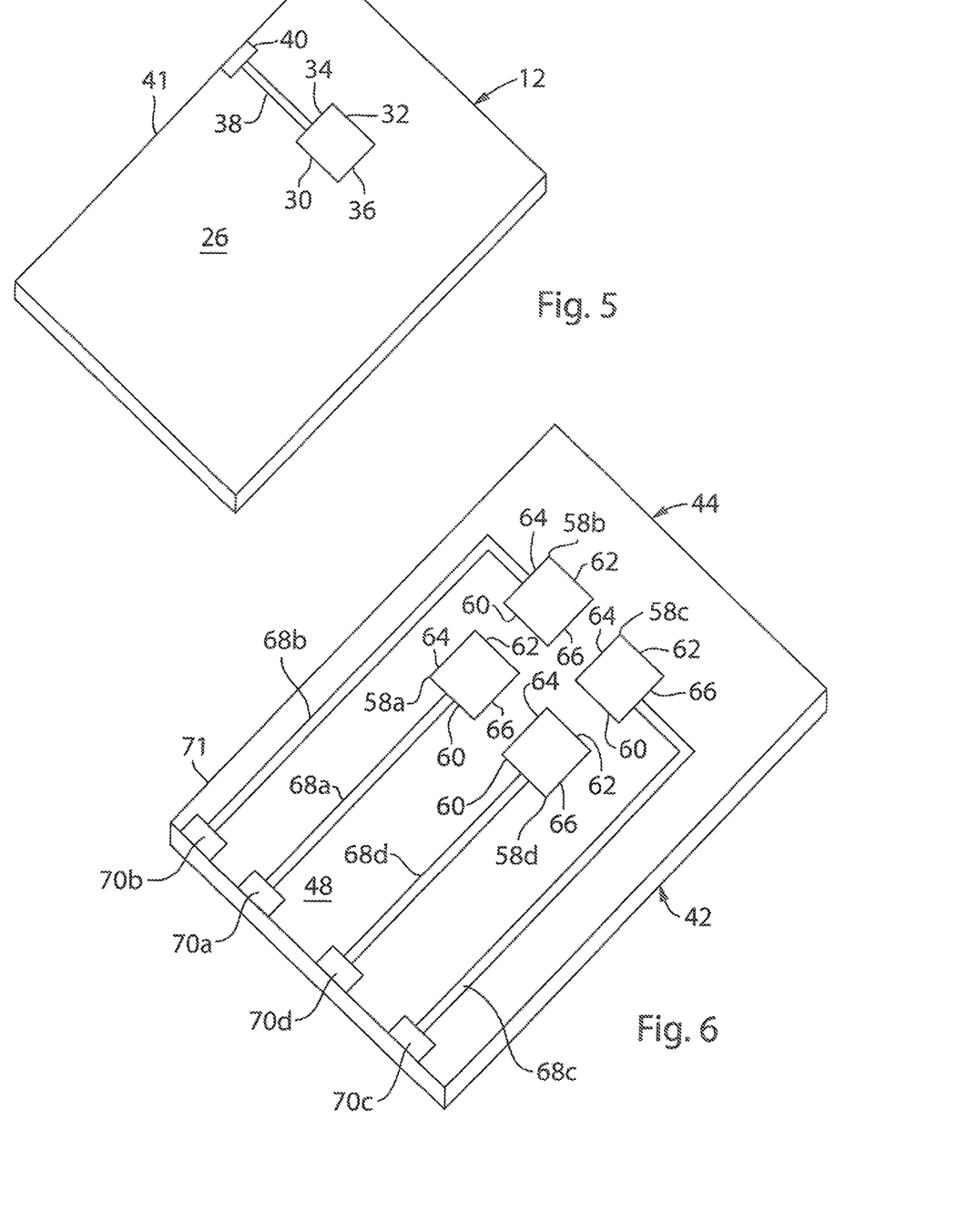
FIG. 5 is an isometric view of an upper plate of the capacitive touch sensor of the present invention.
FIG. 6 is an isometric view of a lower plate of the capacitive touch sensor of the present invention.

Referring to FIGS. 3 and 5, touch sensor 10 further includes a lower plate 42. Lower plate 42 is generally planar and perpendicular to a plate axis 43 extending through center 45 of first electrode 28, Lower plate 42 includes base layer 44 fabricated from an insulating material. Base layer 44 includes an outer surface 46 and an inner surface 48. Lower plate 42 includes a plurality of base electrodes, e.g. base electrodes 58a-58d fabricated from a conductor, such as copper, are provided on inner surface 48 of base layer 44. For reasons, hereinafter described, it is contemplated for base electrodes 58a-58d to be circumferentially spaced about plate axis 43. It can be appreciated that the number of base electrodes 58a-58d circumferentially spaced about plate axis 43 may be varied without deviating from the scope of the present invention.

Each base electrode 58a-58d is defined by first and second sides 60 and 62, respectively, and first and second ends, 64 and 66, respectively. In the depicted embodiment, each base electrode 58a-58d has a square con figuration. However, other configurations, e.g, circular configurations, are possible without deviating from the scope of the present invention. Lines 68a-68d and terminals 70a-70d are also provided on inner surface 48 of base layer 44. Lines 68a-68d interconnect terminals 70a-70d to corresponding base electrodes 58a-58d. Terminals 70a-70d are provided adjacent outer periphery 71 of base layer 44 for reasons hereinafter described. Insulating coverlay 47 is provided over on inner surface 48 of base layer 44, base electrodes 58a-58d and lines 68a-68d to prevent short circuits during operation of touch sensor 10, hereinafter described.

Dielectric layer 72 is provided between upper and lower plates 12 and 42, respectively. It is intended for dielectric layer 72 to be deformable so as to allow upper plate 12 (or a portion thereof to move in three dimensions with respect to lower plate 42. More specifically, it is contemplated to fabricate dielectric layer 72 from a plurality of cylindrical posts 74 having circular cross, sections. However, posts 74 may have other configurations without deviating from the scope of the present invention. Each cylindrical post 74 includes an outer surface 76, an upper end 80 bonded to upper plate 12 and a lower end 78 bonded to lower plate 42. It can be appreciated that cylindrical posts 74 have sufficient deformability so as to compress along a y-axis coincident with plate axis 43 in response to a compressive force on upper plate 12 (and hence, first electrode 28) and/or flex along an x-axis, a z-axis or a combination thereof in response to a corresponding shear force on upper plate 12 (an hence, first electrode 28), as hereinafter described, FIGS. 7a, 8a, 9a and 10a.

Figure 2:
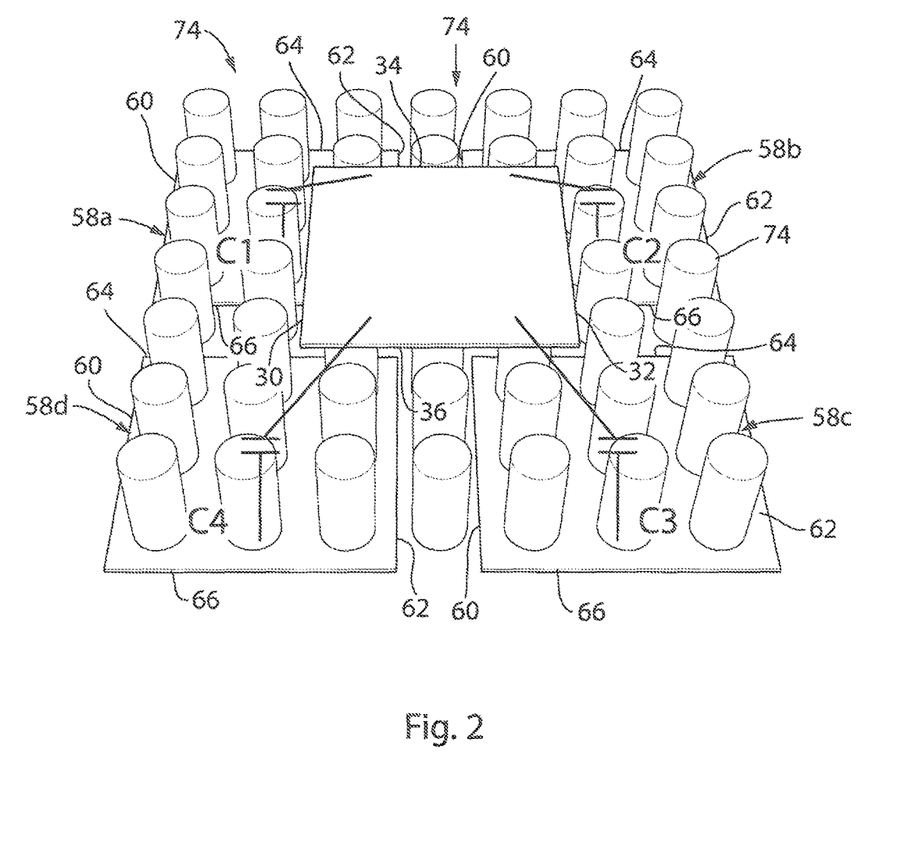
FIG. 2 is a schematic, top elevational view of the capacitive touch sensor of FIG. 1.
Figure 4:
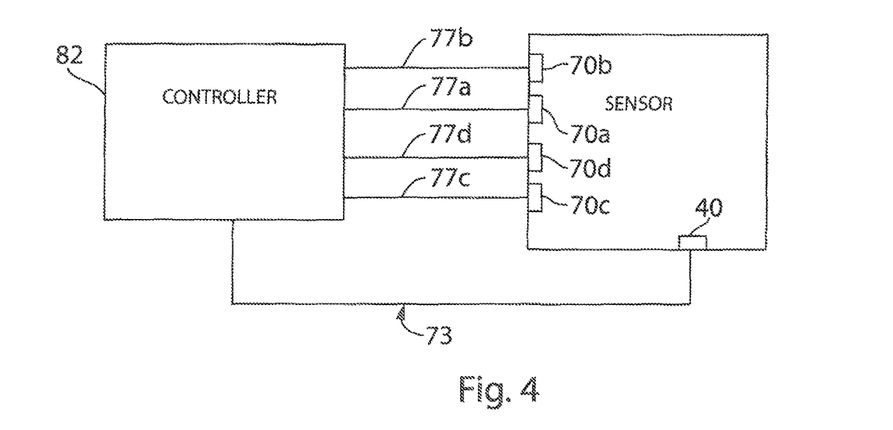
FIG. 4 is a block diagram of the capacitive touch sensor of the present invention operatively connected to a controller.
Figure 8A:
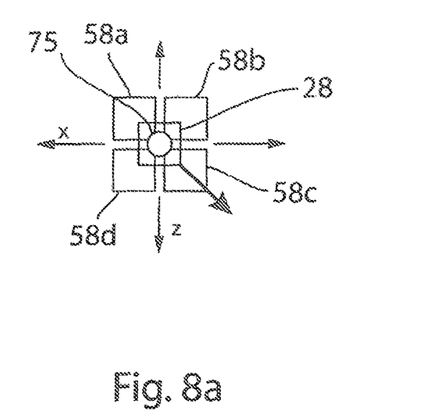
FIG. 8a is a schematic view of the force in a second position engaging the capacitive touch sensor of the present invention.
Figure 9A:
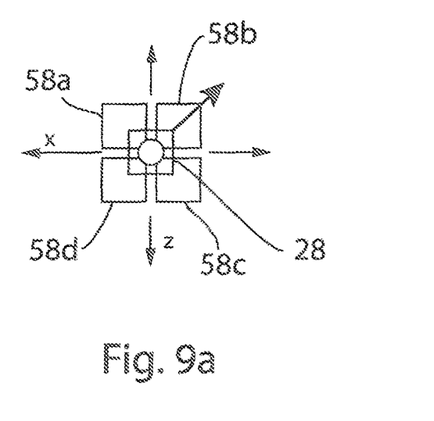
FIG. 9a is a schematic view of the force in a third position engaging the capacitive touch sensor of the present invention.
Figure 10A:
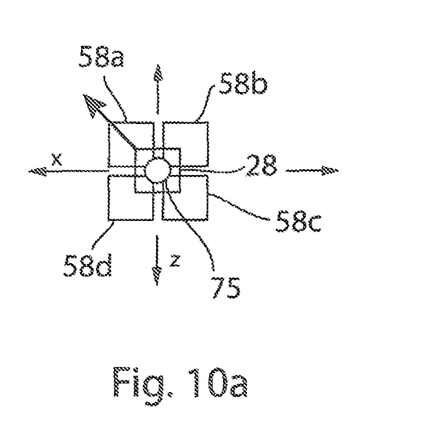
FIG. 10a is a schematic view of the force in a fourth position engaging the capacitive touch sensor of the present invention.

As described, first electrode 28 and each base electrode 58a-58d define a corresponding capacitor having a measureable differential capacitance C1, C2, C3 and C4, respectively, therebetween, FIG. 2. The differential capacitances between first electrode 28 and each base electrode 58a-58d are monitored by controller 82 which is operatively connected to terminal 40 by line 73 and to terminals 70a-70d by, lines 77a-77d, respectively, FIG. 4. The compression and/or flexing of dielectric layer 72, namely, cylindrical posts 74, in response to a compressive force 75 exerted on upper plate 12 along an axis parallel to plate axis 43, FIG. 7a, and/or a shear force 75 exerted on upper plate 12, FIGS. 8a, 9a and 10a, causes the differential capacitances between first electrode 28 and base electrodes 58a-58d to change. The change in differential capacitances between first electrode 28 and base electrodes 58a-58d is detected by controller 82. More specifically, when a force parallel to plate axis 43 is applied to upper plate 12, FIG. 7a, to cylindrical posts 74 deform so to fill out the air gaps between adjacent cylindrical posts 74. As a result, two effects that contribute to an increase in the differential capacitance between first electrode 28 and each base electrode 58a-58d, namely, the distance between first electrode 28 and each base electrode 58a-58d decreases and the effective permittivity of dielectric layer 72 increases. When a shear force alone or in combination with a compressive force 75 is applied to upper plate 12. FIGS. 8a, 9a and 10a, cylindrical posts 74 flex or move in a direction of the applied shear three and may compress in response to the compressive force. As a result, a larger portion of first electrode 28 overlaps at least one of base electrodes 58a-58d in the direction of applied shear force and a smaller portion of first electrode 28 overlaps the other base electrodes 58a-58d. Hence, the differential capacitance between first electrode 28 and the overlapped base electrodes 58a-58d increases, while the differential capacitance between first electrode 28 and the other base electrodes 58a-58d not in the direction of the shear force applied decreases. The change in differential capacitances between first electrode 28 and base electrodes 58a-58d is detected by controller 82. It can be appreciated that differences in the differential capacitances between first electrode 28 and each base electrode 58a-58d measured by controller 82 may be used to track the magnitude and the trajectory of the force 75 applied to upper plate 12.

In order to validate the performance of differential, capacitance touch sensor 10, an exemplary differential capacitance touch sensor was constructed. In the exemplary differential capacitance touch sensor 10, first electrode 28 was fabricated to be general square and have a length of 7 millimeters (mm) and a width of 7 mm. Similarly, each base electrodes 58a-58d was fabricated to be generally square and have a length of 7 mm and a width of 7 mm. Base electrodes 58a-58d lied in a common plane which was spaced from the plane in which first electrode 28 lies by 2 mm. The edges of each base electrodes 58a-58d are spaced from the edges of adjacent base electrodes 58a-58d by a distance of 4 mm.

Figure 7A:
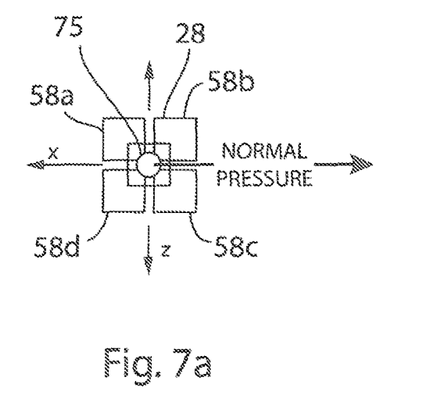
FIG. 7a is a schematic view of a force in a first position engaging the capacitive touch sensor of the present invention.
Figure 7B:
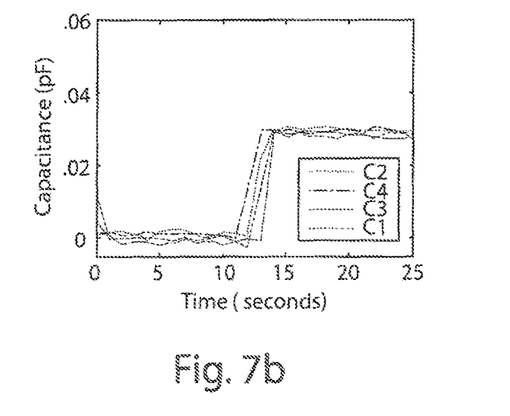
FIG. 7b is a graphical representation of measured differential capacitances between a first electrode and four base electrodes of the capacitive touch sensor of the present invention in response to the force in the first position engaging the capacitive touch sensor.
Figure 8B:
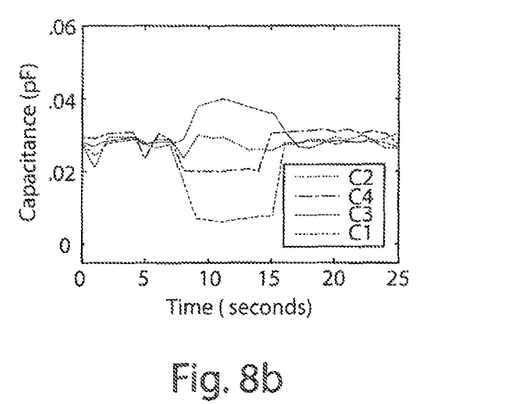
FIG. 8b is a graphical representation of measured differential capacitances between the first electrode and the four base electrodes of the capacitive touch sensor of the present invention in response to the force in the second position engaging the capacitive touch sensor.

In operation, a constant force 75 of approximately 0:17 Newtons (N) was applied to outer surface 16 of upper plate 12 along an axis coincident with plate axis 43, FIG. 7a. As best seen in FIG. 7b, the differential capacitance between first electrode 28 and each of base electrodes 58a-58d increased approximately 0:3 picofarads (pF). As force 75 applied to upper plate 12 moves along outer surface 16 in a direction so as to overlap base electrode 58c, FIG. 8a. the differential capacitance between first electrode 28 and base electrode 58c increases, the differential capacitance between first electrode 28 and is base electrodes 58b and 58d remain relatively constant and the differential capacitance between first electrode 28 and base electrode 58a decreases, FIG. 8b. The decrease in the differential capacitance value between first electrode 28 and base electrode 58a is a result of the increase in the distance between first electrode 28 and base electrode 58a, while the increase in differential capacitance between first electrode 28 and base electrode 58c is due to the increase in the overlap area between first electrode 28 and base electrode 58c in the direction of the motion.

Figure 9B:
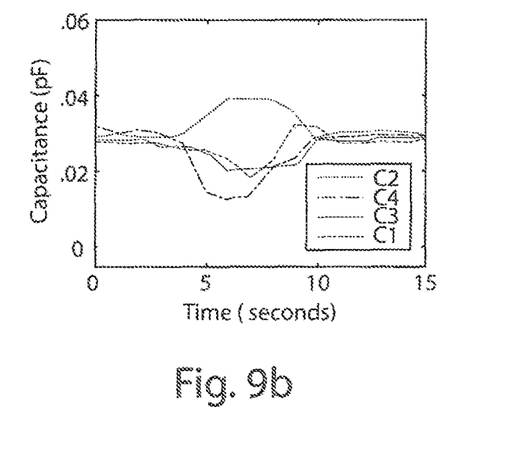
FIG. 9b is a graphical representation of measured differential capacitances between the first electrode and the four base electrodes of the capacitive touch sensor of the present invention in response to the force in the third position engaging the capacitive touch sensor.

Similarly, as force 75 applied to upper plate 12 moves along outer surface 16 in a direction so as to overlap base electrode 58b, FIG. 9a, the differential capacitance between first electrode 28 and base electrode 58b increases, the differential capacitances between first electrode 28 and base electrodes 58a and 58c approach their initial differential capacitances of 0:3 pF, and the differential capacitance between first electrode 28 and base electrode 58d decreases, FIG. 9b. The decreases in the differential capacitance values between first electrode 28 and base electrode 58c and between first electrode 28 and base electrode 58d are a result of the increase in the distance between first electrode 28 and base electrodes 58c and 58d, while the increase in differential capacitances between first electrode 28 and base electrode 58a and between first electrode 28 and base electrode 58b are due to the increase in the overlap areas between first electrode 28 and base electrode 58a and between first electrode 28 and base electrode 58b in the direction of the motion.

Figure 10B:
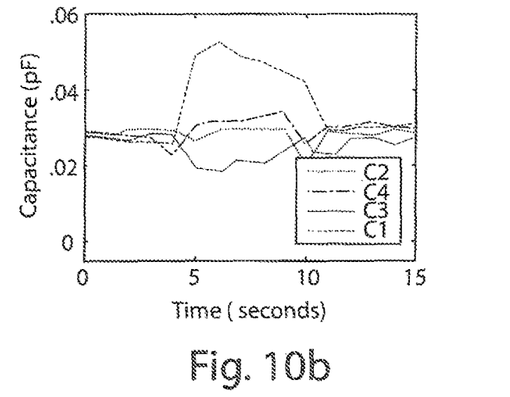
FIG. 10b is a graphical representation of measured differential capacitances between the first electrode and the four base electrodes of the capacitive touch sensor of the present invention in response to the force in the fourth position engaging the capacitive touch sensor.

In a similar manner, as force 75 applied to upper plate 12 moves along outer surface 16 in a direction so as to overlap base electrode 58a, FIG. 10a, the differential capacitance between first electrode 28 and base electrode 58a increases, the differential capacitances between first electrode 28 and base electrodes 58b and 58d approach their initial differential capacitances of 0:3 pF, and the differential capacitance between first electrode 28 and base electrode 58c decreases, FIG. 10b. The decreases in the differential capacitance values between first electrode 28 and base electrode 58b and between first electrode 28 and base electrode 58c are a result of the increase in the distance between first electrode 28 and base electrodes 58b and 58c, while the increase in differential capacitances between first electrode 28 and base electrode 58a and between first electrode 28 and base electrode 58d are due to the increase in the overlap areas between first electrode 28 and base electrode 58c and between first electrode 28 and base electrode 58d in the direction of the motion.

It can be appreciated that if force 75 applied to upper plate 12 moves along outer surface 16 in a direction so as to overlap base electrode 58d, the differential capacitance between first electrode 28 and base electrode 58d would increases the differential capacitances between first electrode 28 and base electrodes 58a and 58c would approach their initial differential capacitances of 0:3 pF, and the differential capacitance between first electrode 28 and base electrode 58b would decrease. The decreases in the differential capacitance values between first electrode 28 and base electrode 58a and between first electrode 28 and base electrode 58b would be a result of the increase in the distance between first electrode 28 and base electrodes 58a and 58b, while the increase in differential capacitances between first electrode 28 and base electrode 58c and between first electrode 28 and base electrode 58d would be due to the increase in the overlapping areas between first electrode 28 and base electrode 58c and between first electrode 28 and base electrode 58d in the direction of the motion of force 75.

Referring back to FIG. 4, the changes in differential capacitance may be detected by controller 82, as heretofore described, along with the accompanying variation in signal patterns as a result of the movement of force 75 along outer surface 16 of upper plate 12. Controller 82 may then be utilize such information to quantify the magnitude of the pressure exerted on upper plate 12 by force 75 and track directional motion of force 75 along outer surface 16 of upper plate 12.

Various modes of carrying out the invention are contemplated as being within the scope of the following claims particularly pointing and distinctly claiming the subject matter that is regarded as the invention.

We claim:

1. A capacitive touch sensor, comprising:
a plate having an upper surface and lying in a plate plane;
a planar, first electrode spaced from the plate along an axis perpendicular to the upper surface of the plate, the first electrode movable in three dimensions with respect to the plate in response to a force having a magnitude and a trajectory applied to the first electrode; and
a plurality of second electrodes interconnected to the plate and circumferentially spaced about the axis, each of the plurality of the second electrodes having a corresponding differential capacitance with the first electrode such that the differential capacitances between the first electrode and the plurality of second electrodes vary in the response to a movement of the first electrode; and
a controller operatively connected to the first electrode and the plurality of second electrodes for detecting variances in the differential capacitances, the controller configured to quantify the magnitude and calculate the trajectory of the force on the first electrode in response to the variances in the differential capacitances.

2. The capacitive touch sensor of claim 1 further comprising a dielectric layer extending between the plate and the first electrode.

3. The capacitive touch sensor of claim 2 wherein the dielectric layer includes a plurality of dielectric posts.

4. The capacitive touch sensor of claim 3 wherein the dielectric posts flex in a direction corresponding to the trajectory of the force applied to the first electrode.

5. The capacitive touch sensor of claim 1 wherein each of the plurality of second electrodes is flat and lies in an electrode plane parallel to the plate plane.

6. The capacitive touch sensor of claim 5 wherein each of the plurality of second electrodes has a square configuration.

7. The capacitive touch sensor of claim 5 wherein at least a portion of the first electrode is moveable in an x-direction, a y-direction and a z-direction, wherein:
the y-direction is parallel to axis;
the x-direction is perpendicular to the y-direction; and
the z-direction is perpendicular to the x-direction and the y-direction.

8. The capacitive touch sensor of claim 5 wherein at least a portion of the first electrode is moveable in an x-direction, a y-direction and a z-direction, wherein:
the y-direction is parallel to axis;
the x-direction is perpendicular to the y-direction; and
the z-direction is perpendicular to the x-direction and the y-direction.

9. The capacitive touch sensor of claim 1 wherein each electrode of the first set of electrodes is flat and lies in an electrode plane parallel to the plate plane.

10. The capacitive touch sensor of claim 9 wherein each electrode of the first set of electrodes has a square configuration.

11. A capacitive touch sensor, comprising:
a plate lying in a plate plane and having a first set of electrodes supported on an upper surface thereof, each electrode of the first set of electrodes being circumferentially spaced about an axis extending through the plate and being perpendicular to the upper surface;
a planar, first electrode spaced from the plate along the axis, the first electrode:
movable in three dimensions with respect to each electrode of the first set of electrodes in response to a force having a magnitude and a trajectory applied to the first electrode; and
having a corresponding differential capacitance with each electrode of the first set of electrodes;
wherein the differential capacitances between the first electrode and each electrode of the first set of electrodes varies in the response to a movement of the first electrode; and
a controller operatively connected to the first electrode and the first set of electrodes for detecting variances in the differential capacitances, the controller configured to quantify the, magnitude and calculate the trajectory of the force applied to the first electrode in response to variances in the differential capacitances.

12. The capacitive touch sensor of claim 11 further comprising a dielectric layer extending between the plate and the first electrode.

13. The capacitive touch sensor of claim 12 wherein the dielectric layer includes a plurality of dielectric posts.

14. The capacitive touch sensor of claim 13 wherein the dielectric posts flex in a direction corresponding to the trajectory of the force applied to the first electrode.

15. A method of tracking pressure exerted by and locus of movement of a force, comprising the steps:
exerting a pressure on a sensor with the force, the sensor having a variable differential capacitance;
varying the differential capacitance in response to the pressure exerted by the force on the sensor and a locus of movement of the force along the sensor; and
quantifying a magnitude of the pressure exerted on the sensor by the force and calculating a trajectory of the force in response to variances in the differential capacitance.

16. The method of claim 15 wherein the sensor includes:
a plate having an upper surface and lying in a plate plane;
a planar, first electrode spaced from the plate along an axis perpendicular to the upper surface of the plate, the first electrode movable with respect to the plate in response to the force; and
a plurality of second electrodes interconnected to the plate and circumferentially spaced about the axis, each of the plurality of the second electrodes having a corresponding differential capacitance with the first electrode.

17. The method of claim 16 wherein the differential capacitances between the first electrode and each of the plurality of second electrodes vary in response to at the pressure exerted by the force on the first electrode.

18. The method of claim 17 wherein the differential capacitances between the first electrode and each of the plurality of second electrodes vary in response to the locus of movement of the force along the first electrode.

19. The method of claim 16 wherein the sensor further includes a dielectric layer extending between the plate and the first electrode.

20. The method of claim 19 wherein the dielectric layer includes a plurality of dielectric posts.

21. The method of claim 20 comprising the additional steps of flexing the dielectric posts in a direction corresponding to at least one of the pressure exerted by the force on the first electrode and the locus of movement of the force along the first electrode.

22. The method of claim 16 wherein at least a portion of the first electrode is moveable in an x-direction, a y-direction and a z-direction, wherein:
    the y-direction is parallel to axis;
    the x-direction is perpendicular to the y-direction; and
    the z-direction is perpendicular to the x-direction and the y-direction.

* * * * *